(12) United States Patent
Gresham

(10) Patent No.: US 9,119,604 B2
(45) Date of Patent: Sep. 1, 2015

(54) TOOL MEMBER COVER AND COVER DEPLOYMENT DEVICE

(71) Applicant: Covidien LP, Mansfield, MA (US)

(72) Inventor: Richard D. Gresham, Guilford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/904,425

(22) Filed: May 29, 2013

(65) Prior Publication Data

US 2013/0256381 A1  Oct. 3, 2013

Related U.S. Application Data

(63) Continuation of application No. 10/522,914, filed as application No. PCT/US03/24201 on Jul. 31, 2003, now Pat. No. 8,579,937.

(60) Provisional application No. 60/400,328, filed on Jul. 31, 2002.

(51) Int. Cl.
*A61B 17/00* (2006.01)
*A61B 17/068* (2006.01)
*A61B 17/32* (2006.01)
*A61B 17/34* (2006.01)
*A61B 19/00* (2006.01)
*A61B 17/115* (2006.01)
*A61B 19/02* (2006.01)

(52) U.S. Cl.
CPC ......... *A61B 17/00234* (2013.01); *A61B 17/068* (2013.01); *A61B 17/320068* (2013.01); *A61B 17/3431* (2013.01); *A61B 19/40* (2013.01); *A61B 17/1155* (2013.01); *A61B 17/3494* (2013.01); *A61B 2017/00287* (2013.01); *A61B 2017/3435* (2013.01); *A61B 2019/0267* (2013.01); *A61B 2019/4027* (2013.01)

(58) Field of Classification Search
CPC ................ A61B 17/00234; A61B 2017/3431; A61B 2017/3435
USPC .......... 604/263; 606/114, 127, 205–211, 219; 227/175.1–182.1
See application file for complete search history.

(56) References Cited

U.S. PATENT DOCUMENTS

| | | |
|---|---|---|
| 3,388,847 A | 6/1968 | Kasulin et al. |
| 3,552,626 A | 1/1971 | Astafiev |
| 3,638,652 A | 2/1972 | Kelley |
| 3,894,706 A | 7/1975 | Mizusawa |
| 4,198,982 A | 4/1980 | Fortner et al. |
| 4,207,898 A | 6/1980 | Becht |
| 4,227,537 A | 10/1980 | Suciu et al. |

(Continued)

FOREIGN PATENT DOCUMENTS

| | | |
|---|---|---|
| CA | 908529 | 8/1972 |
| DE | 1057729 | 5/1959 |

(Continued)

*Primary Examiner* — Thomas McEvoy

(57) ABSTRACT

A surgical instrument including a tool member cover and a cover deployment device are disclosed. The cover is supported adjacent to or on the tool assembly of the surgical instrument and is movable from a first position in which the tool assembly is uncovered to a second position in which the tool assembly is at least partially encompassed by the cover. The deployment device is provided for moving the cover from the first position to the second position.

19 Claims, 11 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,657,020 A | 4/1987 | Lifton |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,754,909 A | 7/1988 | Barker et al. |
| 4,817,847 A | 4/1989 | Redtenbacher et al. |
| 4,873,977 A | 10/1989 | Avant et al. |
| 4,877,033 A | 10/1989 | Seitz, Jr. |
| 4,893,662 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Taheri |
| 5,047,039 A | 9/1991 | Avant et al. |
| 5,061,246 A | 10/1991 | Anapliotis |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,285,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,318,221 A | 6/1994 | Green et al. |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,370,647 A | 12/1994 | Graber et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hooven et al. |
| 5,437,684 A | 8/1995 | Calabrese et al. |
| 5,439,156 A | 8/1995 | Grant et al. |
| 5,441,507 A | 8/1995 | Wilk et al. |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,470,006 A | 11/1995 | Rodak |
| 5,474,223 A | 12/1995 | Viola et al. |
| 5,497,934 A | 3/1996 | Brady et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,632,433 A | 5/1997 | Grant et al. |
| 5,639,008 A | 6/1997 | Gallagher et al. |
| 5,658,300 A | 8/1997 | Bito et al. |
| 5,665,073 A | 9/1997 | Bulow et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,758,814 A | 6/1998 | Gallagher et al. |
| 5,762,604 A | 6/1998 | Kieturakis |
| 5,799,857 A | 9/1998 | Robertson et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,741 A | 2/2000 | Williamson et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 * | 7/2001 | Balazs et al. .................. 606/153 |
| 6,264,086 B1 | 7/2001 | McGuckin, Jr. |
| 6,269,997 B1 | 8/2001 | Balázs et al. |
| 6,279,809 B1 | 8/2001 | Nicolo |
| 6,302,311 B1 | 10/2001 | Adams et al. |
| 6,315,770 B1 * | 11/2001 | de la Torre et al. ............... 606/1 |
| 6,318,765 B1 | 11/2001 | Slais et al. |
| 6,338,737 B1 | 1/2002 | Toledano |
| 6,343,731 B1 | 2/2002 | Adams et al. |
| 6,371,968 B1 * | 4/2002 | Kogasaka et al. ............ 606/190 |
| 6,383,195 B1 | 5/2002 | Richard |
| 6,387,105 B1 | 5/2002 | Gifford, III et al. |
| 6,398,795 B1 | 6/2002 | McAlister et al. |
| 6,402,008 B1 | 6/2002 | Lucas |
| 6,428,556 B1 * | 8/2002 | Chin ........................... 606/198 |
| 6,450,390 B2 | 9/2002 | Heck et al. |
| 6,478,210 B2 | 11/2002 | Adams et al. |
| 6,488,197 B1 | 12/2002 | Whitman |

(56) References Cited

U.S. PATENT DOCUMENTS

| | | |
|---|---|---|
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,623,227 B2 | 9/2003 | Scott et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,716,222 B2 | 4/2004 | McAlister et al. |
| 6,716,233 B1 | 4/2004 | Whitman |
| 6,742,692 B2 | 6/2004 | Hartwick |
| 6,752,822 B2 | 6/2004 | Jespersen |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,971,988 B2 | 12/2005 | Orban |
| 7,398,781 B1 * | 7/2008 | Chin ............................ 128/898 |
| 7,901,416 B2 | 3/2011 | Nolan et al. |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0016583 A1 * | 2/2002 | Cragg ............................ 604/500 |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0099393 A1 * | 7/2002 | Fleischman et al. .......... 606/153 |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0139767 A1 | 7/2003 | Jespersen |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0051597 A1 | 3/2005 | Toledano |
| 2005/0067454 A1 | 3/2005 | Vresh et al. |
| 2005/0087580 A1 | 4/2005 | Orban, III |
| 2005/0107813 A1 | 5/2005 | Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2008/0306333 A1 | 12/2008 | Chin |

FOREIGN PATENT DOCUMENTS

| | | |
|---|---|---|
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| EP | 0505138 | 9/1992 |
| FR | 1461464 | 12/1966 |
| FR | 1588250 | 4/1970 |
| FR | 1136020 | 12/1979 |
| FR | 2443239 | 12/1979 |
| GB | 1185292 | 3/1970 |
| GB | 2016991 | 9/1979 |
| GB | 2070499 | 9/1981 |
| NL | 7711347 | 10/1977 |
| WO | 8706448 | 11/1987 |
| WO | 8900406 | 1/1989 |
| WO | 9006085 | 6/1990 |
| WO | WO02/056754 | 7/2002 |
| WO | WO02/087447 | 11/2002 |

* cited by examiner

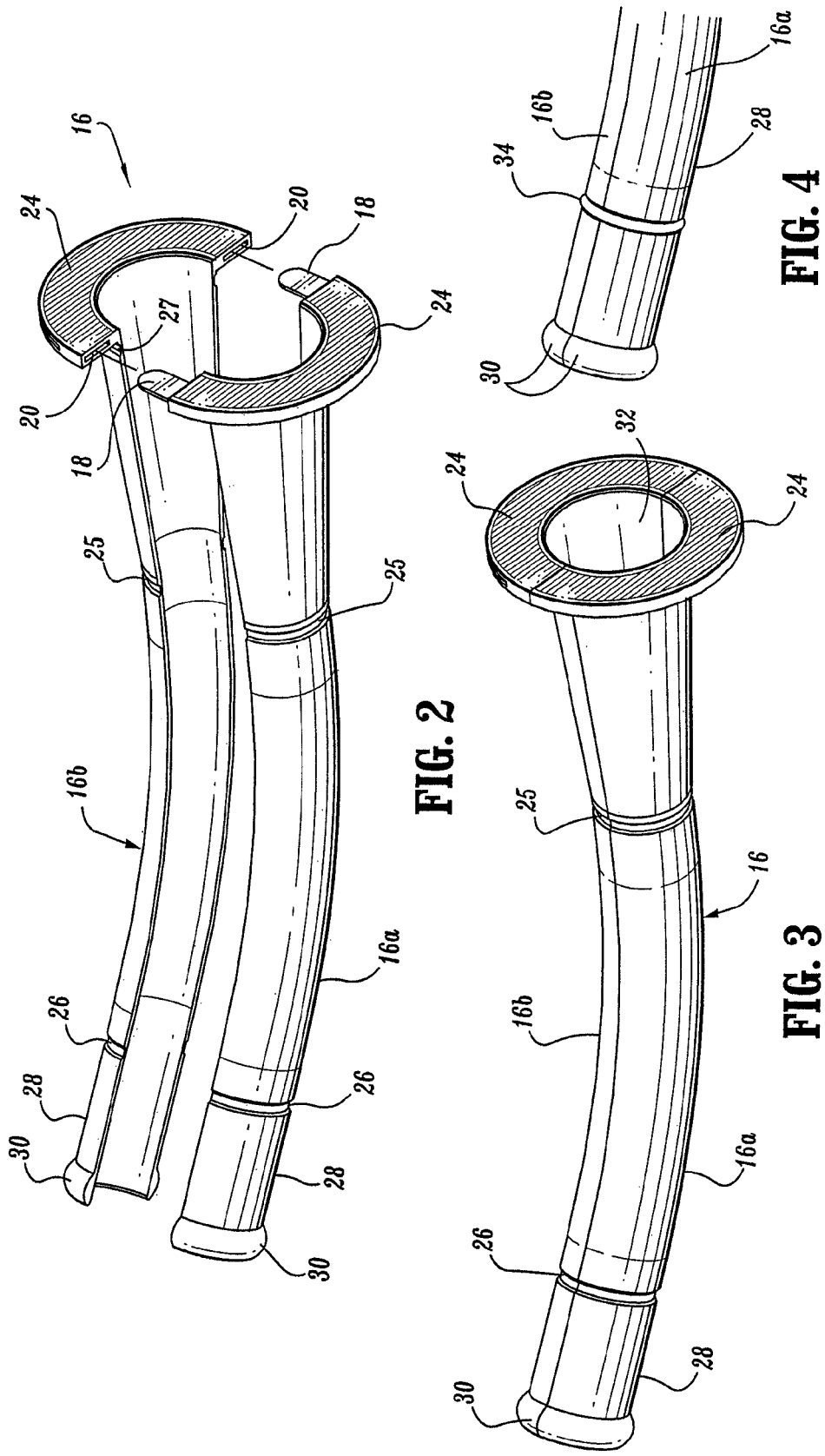

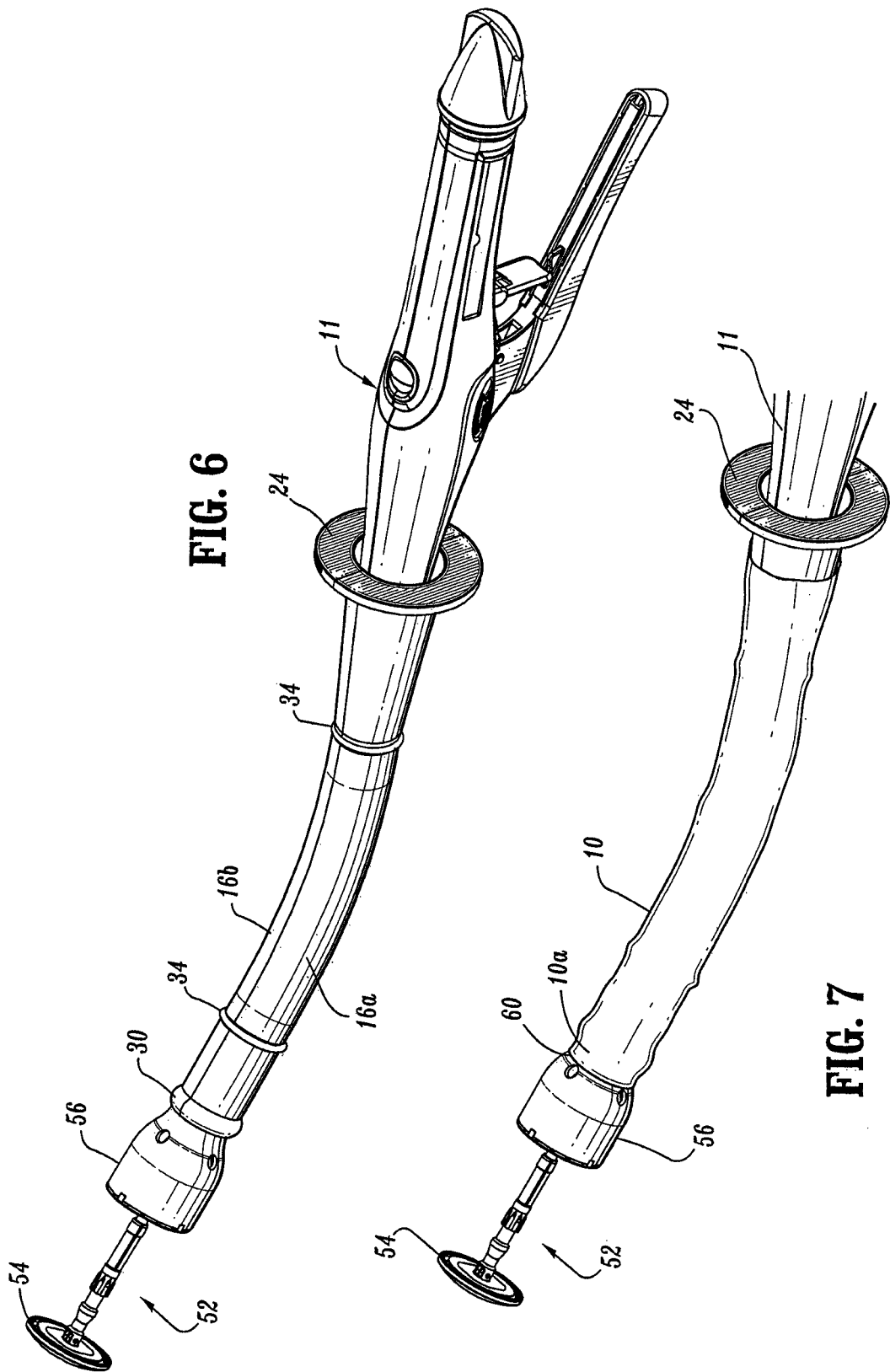

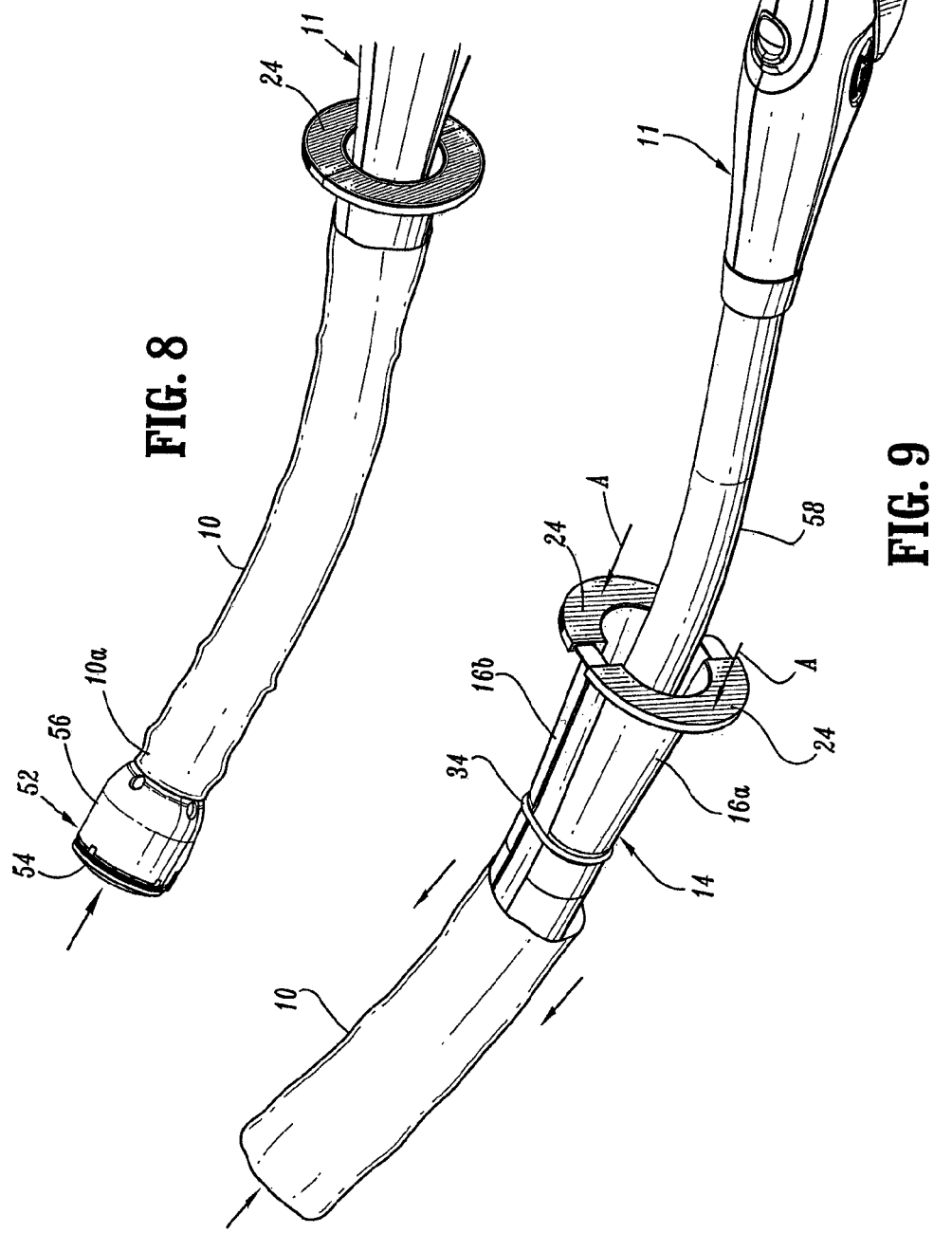

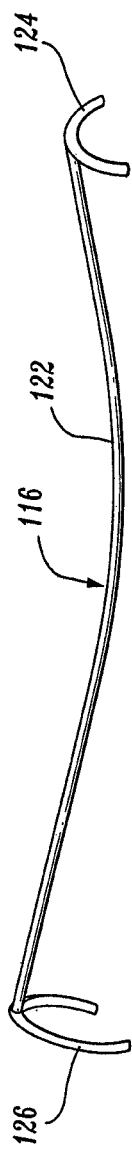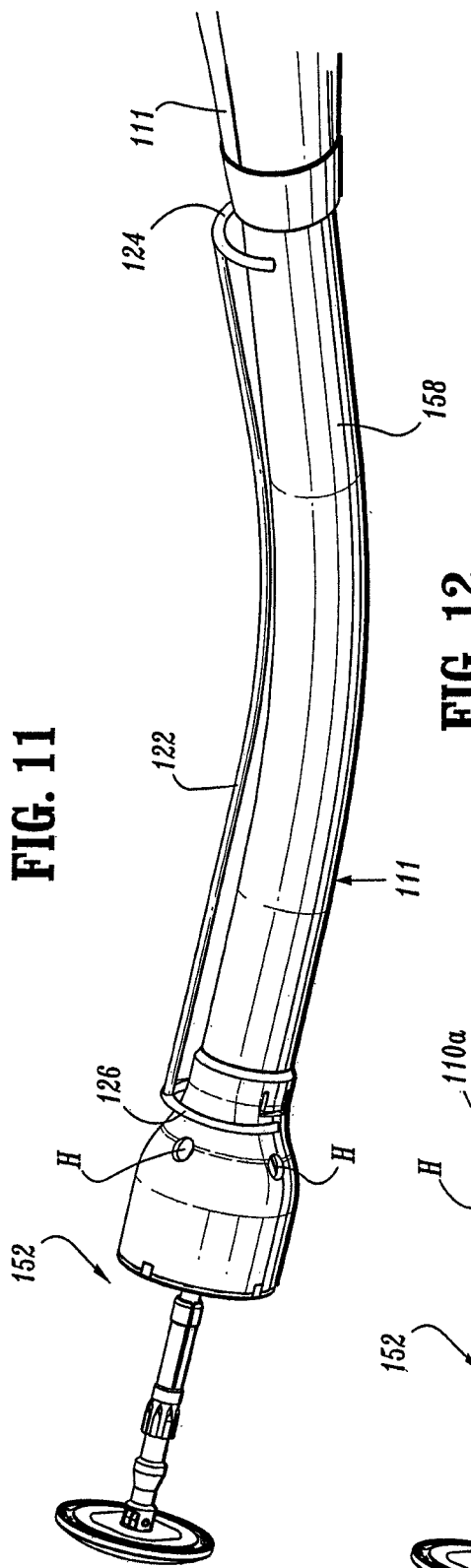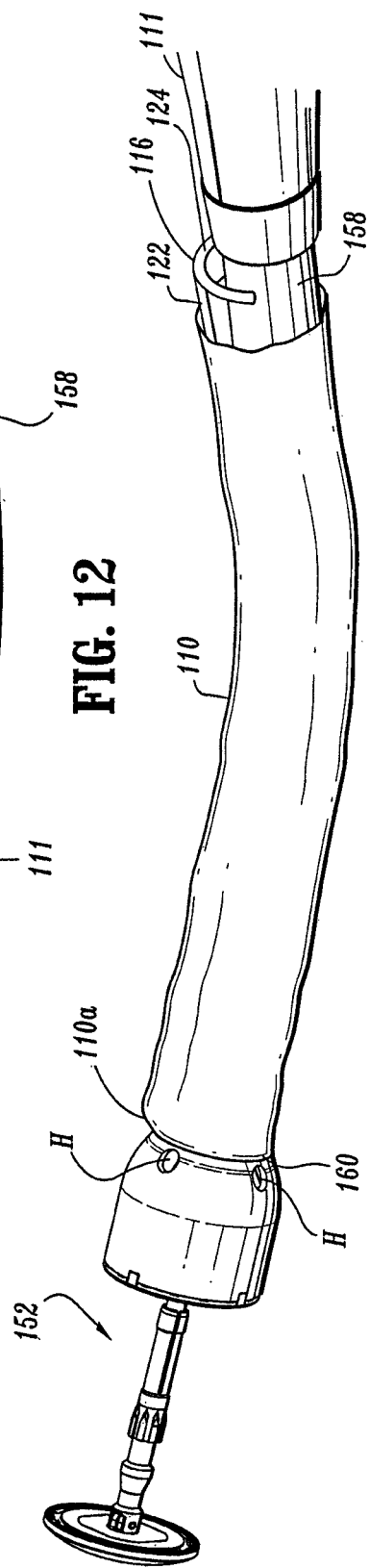
FIG. 11
FIG. 12
FIG. 13

TOOL MEMBER COVER AND COVER DEPLOYMENT DEVICE

CROSS-REFERENCE TO RELATED APPLICATIONS

This application is a continuation of U.S. application Ser. No. 10/522,914 filed Jan. 28, 2005, which is a 371 of application No. PCT/US03/24201 filed Jul. 31, 2003, which claims the benefit of and priority to U.S. Provisional Application Ser. No. 60/400,328, filed Jul. 31, 2002, the entire contents of which are incorporated herein by reference.

BACKGROUND

1. Technical Field

This application relates to a cover and cover deployment device for the tool member or tool assembly of a surgical instrument, and more particularly, to a cover and cover deployment device for the tool member of a laparoscopic or endoscopic surgical instrument for manipulating, treating or excising tissue, especially diseased or cancerous tissue, from a body cavity.

2. Background of Related Art

A variety of different types of surgical instruments have been developed for manipulating, identifying, treating, repairing and/or excising tissue including organs or portions thereof located within body cavities such instruments sometimes being hereafter referred to as surgical instruments for treatment of body tissues. These instruments include graspers, fasteners, e.g., staplers, dissectors, biopsy devices, coagulators, etc. Typically, these instruments are dimensioned to be used in both open and laparoscopic or endoscopic procedures.

In endoscopic surgical procedures for treatment of body tissue, a surgical instrument is inserted through an incision or cannula to a position adjacent the tissue to be treated. The distal tool member of the instrument is then manipulated to treat, i.e., biopsy, excise, dissect, coagulate, reposition, etc., the tissue. Thereafter, the instrument with or without excised tissue is withdrawn from the surgical site through the incision to remove the instrument from the body cavity.

One problem associated with current surgical devices is that during removal of the tool member from the surgical site, the tool member or tool assembly (hereafter, for simplicity "tool member") of the surgical instrument for treating, for example, diseased, tissue comes into contact with the healthy tissue defining the incision and/or within the body cavity in which the surgical site is located. This may also be a problem in open surgical procedures. Where the tissue being treated is diseased tissue, e.g., cancerous, this problem becomes critical since contact between the cancerous tissue and the healthy tissue may result in seeding of cancerous cells resulting in metastases.

Accordingly, a need exists in the art for improved instrumentation for shielding healthy tissue from diseased tissue during removal of a surgical instrument from a surgical site.

SUMMARY

The present disclosure provides a tool member cover for use with a surgical instrument having a tool assembly and a body portion. The cover is preferably tubular and has open distal and proximal ends. A portion of the cover, preferably the distal end, is fastened to the surgical instrument adjacent to or on the tool assembly. Alternately, the cover may be removably attached to the surgical instrument. The cover is movable from a first position in which the tool member is uncovered to a second position in which the cover at least partially encompasses the tool member.

Preferably, the cover is formed of an impermeable material. A deployment device is provided for moving the cover from the first position to the second position. In a first embodiment, the deployment device includes a sleeve formed of half-sections which are held together using expandable members, e.g., resilient O-rings. The O-rings allow the sleeve half-sections to move outwardly relative to each other to allow the sleeve to pass over a tool assembly having a larger diameter than a body portion of the surgical instrument. The sleeve is slidably positioned about the body of a surgical instrument between retracted and advanced positions to move the cover from the first position to the second position. The cover is positioned about the body portion of the surgical instrument and about the deployment device such that when the deployment device is moved from the retracted to the advanced position, the distal end of the sleeve engages the distal end of the cover to invert the cover over the tool assembly.

The cover may include a closure device such as a drawstring or elastic band to close the distal end of the cover to enclose the tool member within the cover. The cover may be used with a variety of different types of surgical instruments including staplers, fasteners, manipulators, biopsy devices, retractors, coagulators, dissectors etc.

BRIEF DESCRIPTION OF THE DRAWINGS

Various preferred embodiments of the presently disclosed tool member cover and cover deployment device are described herein with reference to the drawings, wherein:

FIG. 2 is a side perspective view of the deployment device sleeve with parts separated of the deployment device shown in FIG. 1;

FIG. 3 is a side perspective view of the deployment device sleeve shown in FIG. 2;

FIG. 4 is a perspective cutaway view of the distal end of the deployment device sleeve shown in FIG. 3 fastened together with an O-ring;

FIG. 6 is a side perspective view of the deployment device of FIG. 5 in a contracted configuration, shown positioned about the body portion of an unapproximated circular surgical stapler;

FIG. 7 is a side perspective view of the tool member cover and cover deployment device of FIG. 1 positioned about the body portion of an unapproximated circular surgical stapler with the cover and deployment device in a retracted position and the deployment device in a contracted configuration;

FIG. 8 is a side perspective view of the tool member cover and cover deployment device of FIG. 7 positioned about the body portion of an approximated circular surgical stapler with the cover and deployment device in a retracted position and the deployment device in a contracted configuration;

FIG. 9 is a side perspective view of the tool member cover and cover deployment device of FIG. 7 positioned about the body portion and tool assembly of a circular surgical stapler with the cover and deployment device in a partially advanced position and the deployment device in an expanded configuration;

FIG. 11 is a side perspective view of another preferred embodiment of the presently disclosed cover deployment device;

FIG. 12 is a side perspective view with portions broken away of the cover deployment device shown in FIG. 11 supported on a body portion of an unapproximated circular surgical stapler;

FIG. 13 is a side perspective view with portions broken away of the tool member cover and cover deployment device shown in FIG. 12 supported on a body portion of an unapproximated circular surgical stapler with the deployment device and cover in retracted positions;

DETAILED DESCRIPTION OF PREFERRED EMBODIMENTS

Figure 1:
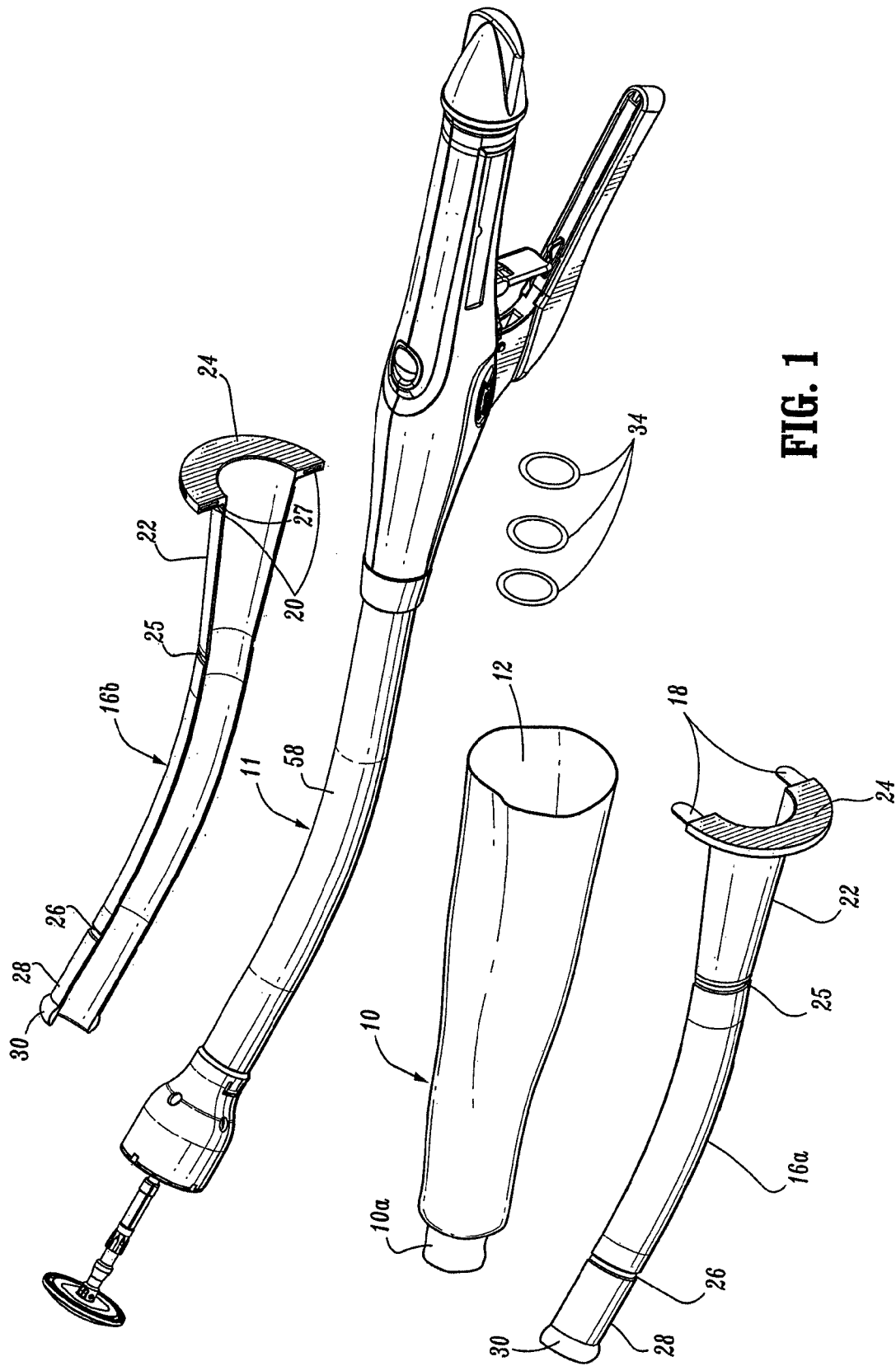
FIG. 1 is a perspective view of one preferred embodiment of the presently disclosed tool member cover and cover deployment device, with parts separated, positioned about an unapproximated circular surgical stapler.

Preferred embodiments of the presently disclosed tool member cover and cover deployment device will now be described in detail with reference to the drawings in which like reference numerals designate identical or corresponding elements in each of the several views.

FIG. 1 illustrates one preferred embodiment of the presently disclosed tool member cover and cover deployment device. Briefly, tool member cover 10 includes a collapsible flexible material which is preferably liquid impermeable and formed from one or more layers of a suitable plastic, preferably, polyethylene. Alternately, other liquid impermeable materials, woven or non-woven, natural or synthetic, and suitable for surgical use may be used to construct the cover, e.g., rubber, elastomers, polytetrafluroethylene, etc. Cover 10 is preferably tubular and defines a lumen 12 dimensioned or configured to receive the body portion 58 of a surgical instrument 11. Preferably, but not necessarily, the distal end 10a of cover 10 has a smaller diameter than the proximal end of cover 10. A portion of cover 10 is preferably fastened to the surgical instrument. The distal end 10a of cover 10 is dimensioned or configured to be fastened directly onto or adjacent to a tool member 52 or a shaft that adjoins a tool member or a handle of a surgical instrument 11. Alternately, cover 10 may have a constant diameter along its entire length or the proximal end of cover 10 may have a smaller diameter than the distal end of cover 10. Cover 10 is preferably fastened to the surgical instrument in a liquid impermeable manner. Cover 10 may also be removably attached to the surgical instrument.

Referring also to FIGS. 2-4, cover deployment device 14 (FIG. 5) includes a sleeve 16 formed of sleeve half-sections 16a and 16b. Sleeve half-section 16a includes a pair of extensions 18 which are dimensioned to be slidably received within slots 20 formed in sleeve 16b. Each sleeve half-section 16a and 16b includes a proximal end 22 having a flange or semi-annular ring 24, a centrally positioned semi-annular recess 25, a distally positioned semi-annular recess 26 and a proximally positioned semi-annular recess 27. The distal end 28 of each sleeve 16a and 16b includes a semi-annular blunt protrusion 30. The function of protrusion 30 will be discussed in detail hereinbelow.

Referring to FIGS. 2-4, sleeve half-sections 16a and 16b are positioned in abutting relationship, with extensions 18 slidably positioned in slots 20 to define a lumen 32 dimensioned to slidably receive or be positioned about a portion of the body of surgical instrument 11. An expandable member, preferably resilient O-ring 34 (FIG. 1), is positioned in each of annular recesses 25, 26 and 27. O-rings 34 are stretchable from a contracted position to an expanded position to allow sleeve half-sections 16a and 16b to move in relation to each other between contracted and expanded positions (FIGS. 3, 4 and 9, respectively). In the contracted position, sleeves 16a and 16b are preferably held in abutting relation with extensions 18 fully inserted within slots 20.

Figure 5:
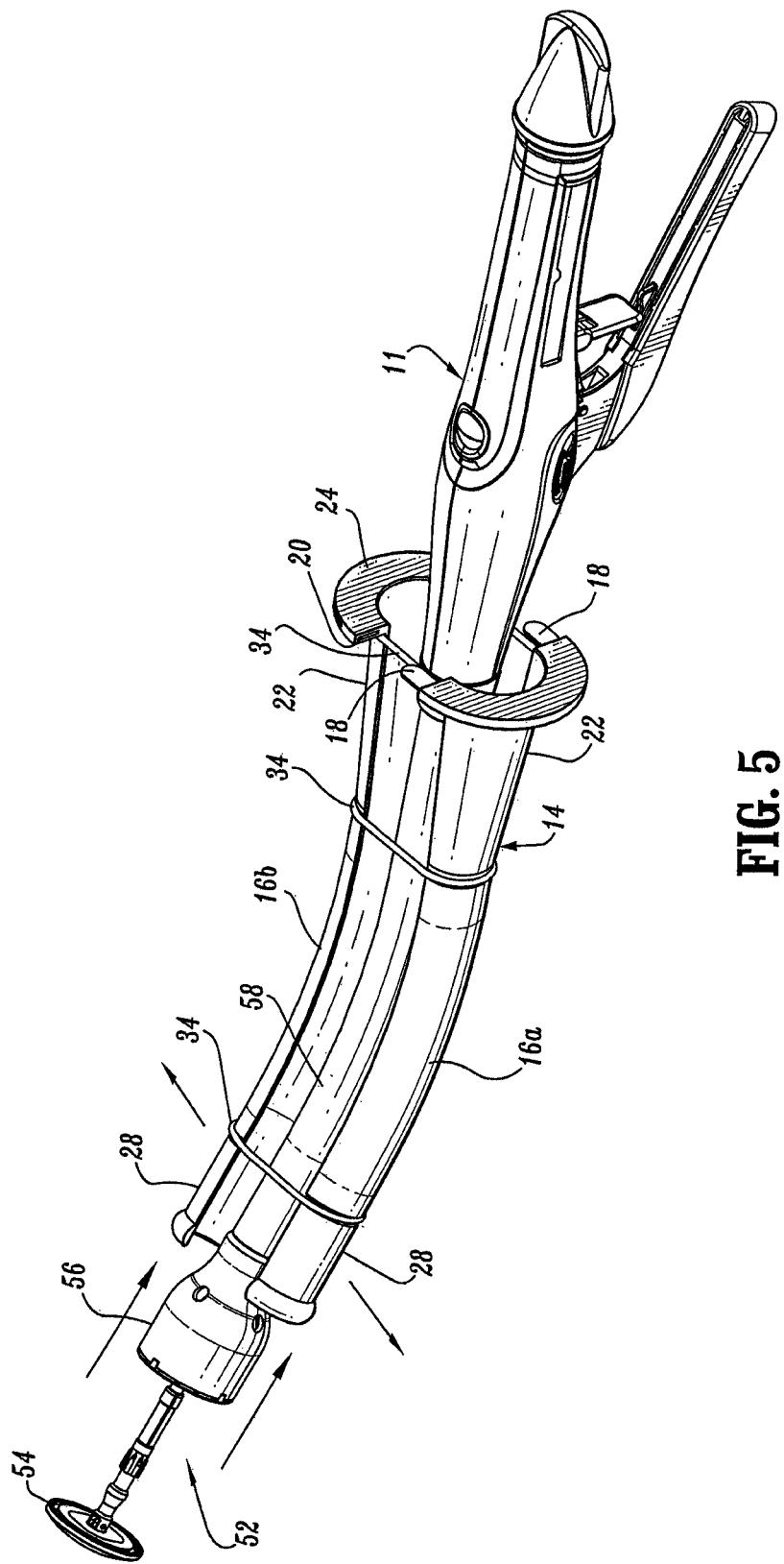
FIG. 5 is a perspective view of the deployment device shown in FIG. 3 positioned about the body portion of an unapproximated circular surgical stapler with the sleeve halves in an expanded configuration.

Referring to FIG. 5, sleeve half-sections 16a and 16b are configured to be easily assembled about the elongated body portion 58 of surgical instrument 11 such that the distal end 28 of sleeve 16 is positioned adjacent a tool assembly 52 of surgical instrument 11. Although surgical instrument 11 is illustrated as a circular stapler, it is envisioned that the surgical instrument may be any of a wide variety of instruments for performing a wide variety of functions including cutting, fastening, manipulating, treating, dissecting, coagulating and biopsing tissue. Such instruments include retractors, biopsy devices, dissectors, coagulators, fasteners, staplers, including linear staplers, circular stapler, semi-circular staplers, arc shaped staplers, etc.

Referring also to FIGS. 6 and 7, in the illustrated embodiment, circular stapler 11 includes an unapproximated tool assembly 52 having an anvil 54, a shell assembly 56 and an elongated body 58. One known circular stapler is disclosed in PCT application Serial No. PCT/US02/10792, which is incorporated herein in its entirety by reference. Sleeve 16 is expandably and slidably positioned about elongated body 58 such that protrusion 30 is positioned adjacent to shell assembly 56. The distal end 10a of cover 10 is preferably secured adjacent to or on the proximal portion of tool assembly 52 at a fastening point or securement 60 (FIG. 7) using a known fastening technique, e.g., adhesion, fusion, crimping, pins, clips etc. and is positioned about sleeve 16 and body portion 58 of surgical instrument 11. Alternately, cover 10 may be releaseably secured to the instrument using known techniques including springs, tabs, hooks, etc. Annular protrusion 30, which is formed at the distal end 28 of sleeve 16, is positioned proximally of fastening point or securement 60.

It is understood that cover 10 can be secured at any suitable location along shaft 58, although on some instruments securing it close to or even on the tool member itself will save cover material and will render the cover easier to manipulate with or without tissue therein.

Figure 10:
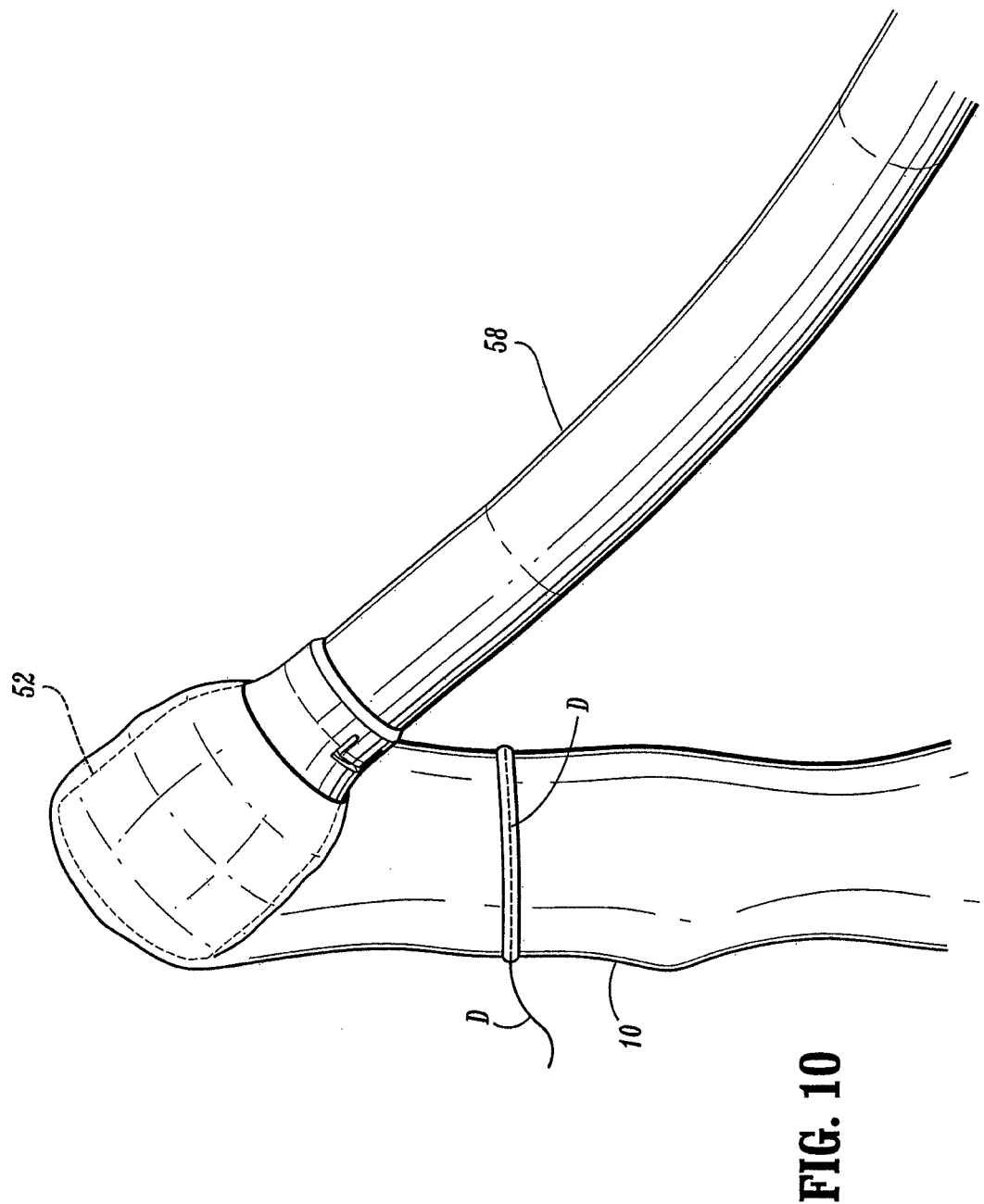
FIG. 10 is a side perspective cutaway view of the tool member cover deployed about the tool member of an approximated circular surgical stapler.

Referring to FIGS. 8-10, in the illustrated embodiment, the distal end 10a of cover 10 is fastened to the proximal portion of shell assembly 56 of tool assembly 52. In use, surgical instrument 11 is positioned such that tool assembly 52 is located adjacent the surgical site. During an endoscopic surgical procedure, this would include inserting the tool assembly 52 and a portion of body portion 58 through an incision with cover 10 and cover deployment device 14 supported about elongated body portion 58 of surgical instrument 11. Thereafter, the surgical instrument is manipulated to perform its associated or designed function. With respect to a circular stapler, body tissue (not shown) is positioned between an unapproximated anvil 54 and shell assembly 56 using, for example, a purse string suture (not shown). Next, the anvil 54 and shell assembly 56 are approximated and surgical instrument 11 is fired in a known manner to dissect tissue and apply a circular array of staples to the dissected and remaining tissue. After surgical instrument 11 has performed its associated function but prior to removal of tool assembly 52 from the surgical site, annular ring 24 of sleeve 16 is pushed forward manually, mechanically, remotely, or robotically in the direction indicated by arrows "A" in FIG. 9 to advance sleeve 16 about body 58 of surgical instrument 11. As sleeve 16 is advanced, annular protrusion 30 engages distal end 10a to invert cover 10 about securement 60 and gradually about cover 10 proximally of secured or attached tool assembly 52. Annular protrusion 30 includes a smooth or blunt surface to prevent tearing of cover 10 during advancement. Because tool assembly 52 has a diameter larger than body 58, at least the distal end portions of sleeve half-sections 16a and 16b expand outwardly in relation to each other by stretching O-rings 34 as distal end 28 of sleeve 16 rides over tool assembly 58. It is noted that in surgical instruments having a tool assembly having a diameter equal to or less than the diameter of the body of the surgical instrument, stretchable o-rings would not be required. When sleeve 16 has been advanced to fully deploy cover 10 about and preferably beyond tool assembly 52 (FIG. 10), the cover deployment device can be withdrawn to its retracted position about body 58 of surgical instrument 11. Surgical instrument 11 including tool assembly 52 and incised tissue therein or thereabout (not shown) and enclosed by cover 10 can now be withdrawn from the surgical site without exposing the healthy tissue defining the incision and within the body cavity (not shown) to diseased tissue on or in the tool assembly.

FIGS. 11-13 illustrate another preferred embodiment of the presently disclosed cover deployment device shown generally as 116. It is noted that the deployment devices disclosed herein are only exemplary embodiments. Any suitable deployment device capable of positioning a cover over a tool assembly of a surgical instrument after it has been used in a surgical procedure is within the scope of this disclosure. Cover deployment device 116 includes a semi-rigid body portion 122 having a proximal semi-annular guide portion 124 and a distal semi-annular engagement member 126. Semi-annular engagement member 126 is preferably formed of a sufficiently, diametrically and radially resilient material and is configured and dimensioned to engage the proximal end of a tool assembly 152 of a surgical instrument 111. Proximal guide portion 124 is configured to partially encompass body portion 158 of surgical instrument 111 and to be pushed by a surgeon to operate deployment device 116. Body portion 122 of deployment device 116 interconnects guide portion 124 and engagement member 126 and is sufficiently rigid to transfer the imparted pushing force to the engagement member 126.

The distal end 110a of cover 110 is secured to surgical instrument 111 adjacent to or on a proximal portion of tool assembly 152 in the manner described above with respect to cover 10, such that cover 110 is positioned about deployment device 116 and body 158 of surgical instrument 111. Engagement member 126 is positioned slightly proximally of a fastening point 160 of cover 110 and to tool assembly 152. In use, deployment device 116 is advanced about body 158 of surgical instrument 111 by pushing on guide portion 124 to advance engagement member 126 into the distal end of cover 110 to invert cover 110 about tool assembly 152 in a manner similar to that disclosed above. Because engagement member 126 is flexible, it is able to slide over the increasing diameter of tool assembly 152. After cover 110 is fully deployed (not shown), deployment device 116 can be retracted and surgical instrument 111 can be removed from a surgical site.

It is to be noted that the distal end 110a of cover 110 can be secured to tool assembly 152 or a similar or like operating end to end anastomosis device that does not require holes such as "H" (FIG. 12) to vent directly to the atmosphere.

Figure 14:
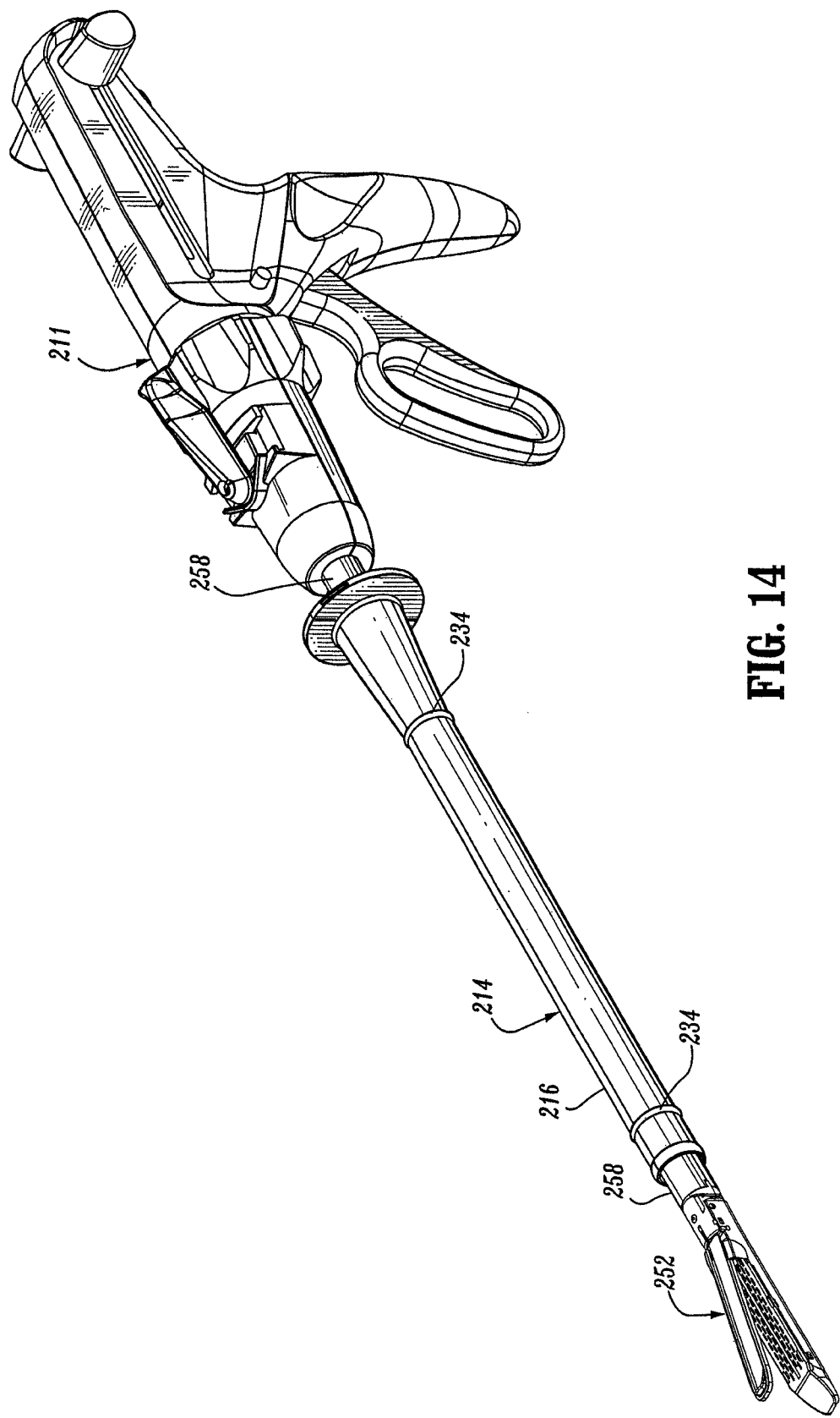
FIG. 14 is a side perspective view of the cover deployment device shown in FIG. 1 positioned about the body portion of endoscopic gastrointestinal anastomosis linear stapler.
Figure 15:
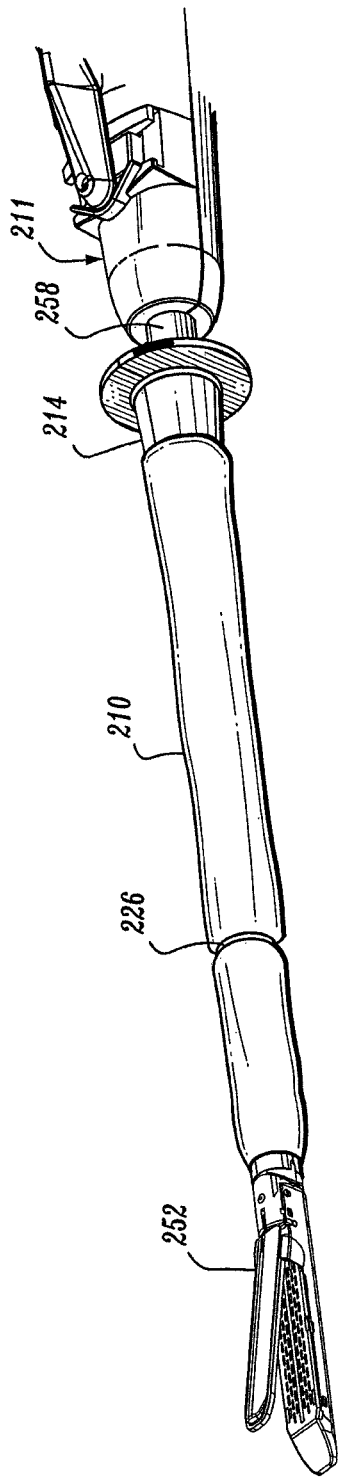
FIG. 15 is a side perspective view with portions broken away of another preferred embodiment of the tool member cover and the cover deployment device shown in FIG. 1 positioned about the body portion of the endoscopic gastrointestinal anastomosis linear stapler of FIG. 15 with the cover and deployment device in retracted positions.
Figure 16:
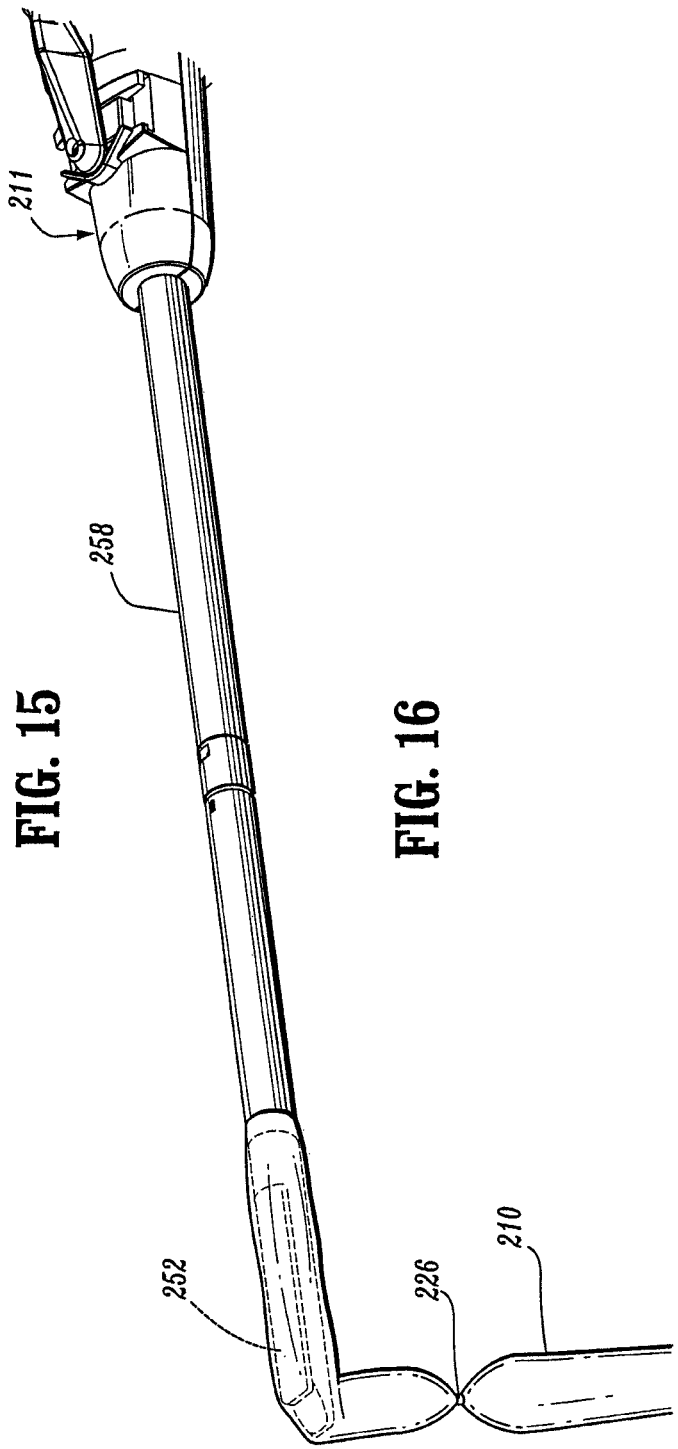
FIG. 16 is a side perspective view of the tool member cover in a deployed configuration positioned about the tool member of the endoscopic gastrointestinal intestinal anastomosis linear stapler of FIG. 15.

FIGS. 14-16 illustrate another preferred embodiment of tool assembly cover 210 and cover deployment device 214 including sleeve 216 positioned about a body portion 258 of an endoscopic gastrointestinal anastomosis linear stapler 211. Such a stapler is described in detail in U.S. Pat. No. 6,241,139 which issued on Jun. 5, 2001 and is incorporated herein in its entirety by reference. The cover deployment device 216 is substantially identical in structure and use as the deployment device described in FIGS. 1-10 and will not be described in further detail herein. Cover 210 is substantially identical to cover 10 described above but further includes an elastic band 226 formed about, within or integrally with a central portion of cover 210. Cover 210 is deployed in a manner substantially identical to that disclosed above. However, as shown in FIG. 16, when elastic band 226 is forced over the distal end of tool assembly 252 of surgical instrument 211, elastic band 226 contracts to close cover 210 about tool assembly 252. The enclosed bag prevents tissue and/or body fluids from escaping cover 210 and infecting healthy tissue in the body cavity or in the incision. It is noted that one or more elastic band(s) 226 may be employed with or incorporated into any of the covers disclosed herein.

Figure 17:
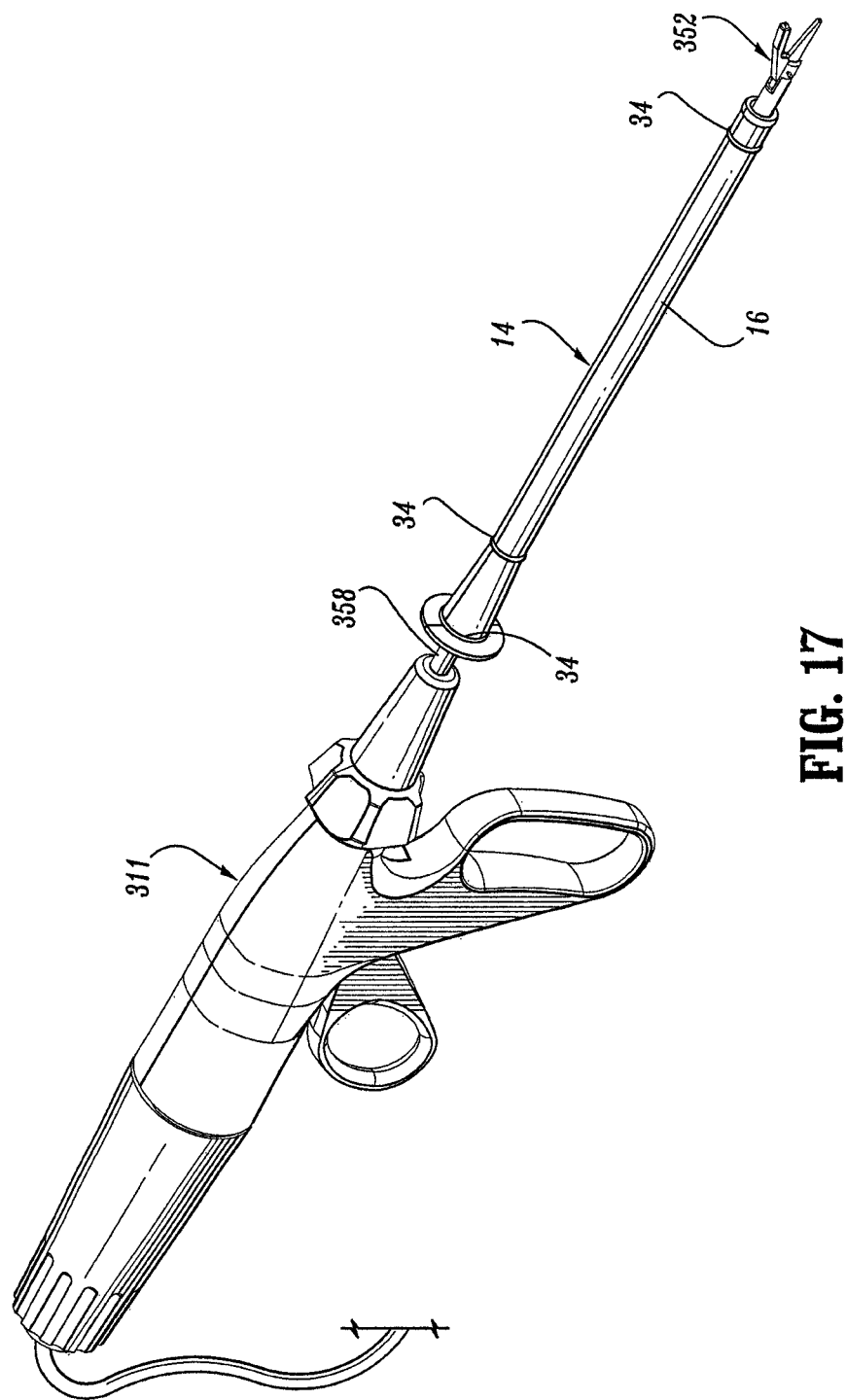
FIG. 17 is a side perspective view of the cover deployment device shown in FIG. 1 positioned about the body portion of an ultrasonic dissection device.
Figure 18:
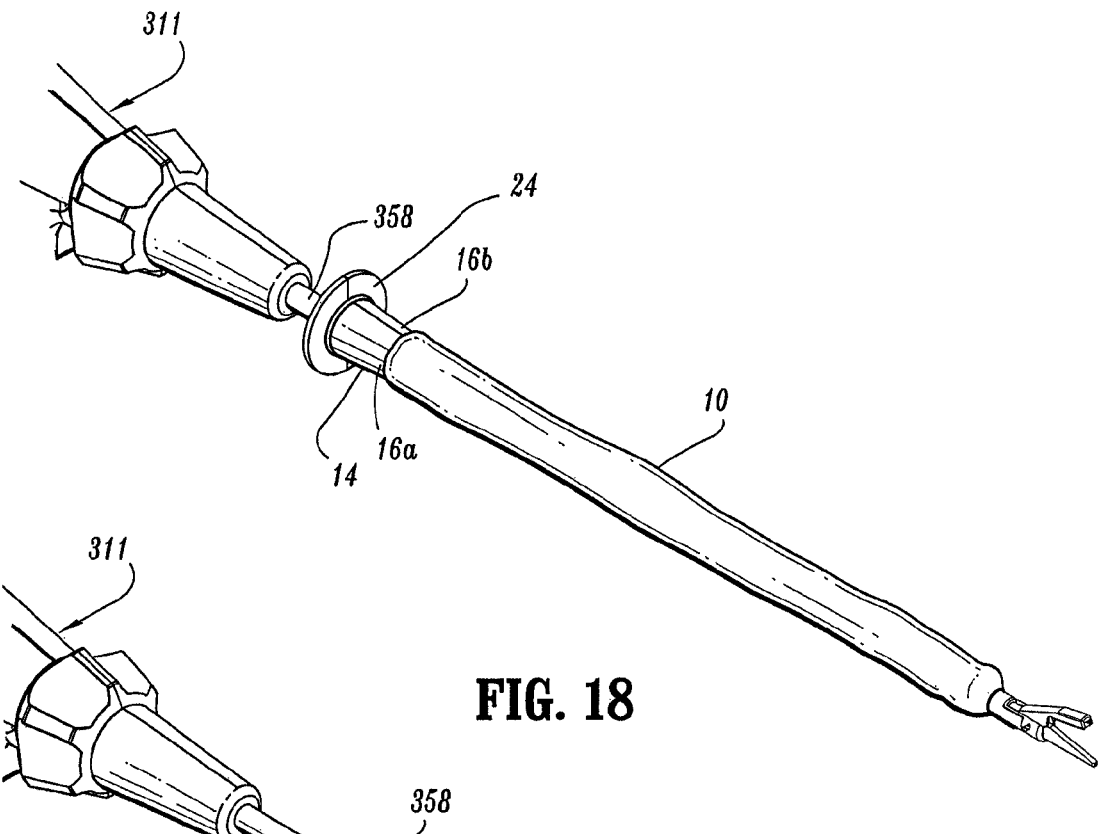
FIG. 18 is a side perspective view of the tool member cover and cover deployment device shown in FIG. 1 positioned about the body portion of the ultrasonic dissection device of FIG. 17 with the tool member cover and deployment device in retracted positions.
Figure 19:
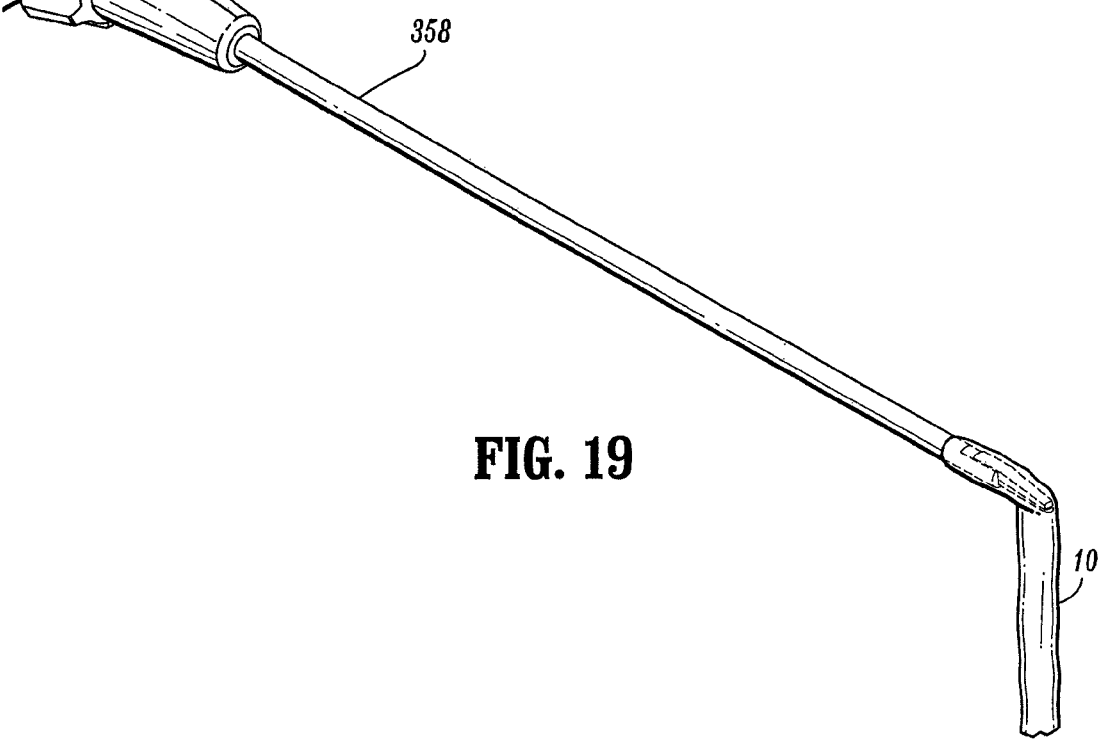
FIG. 19 is a side perspective view of the tool member cover in a deployed configuration about the tool member of the ultrasonic dissection device of FIG. 18.

FIG. 17-19 illustrate tool assembly cover 10 and cover deployment device 14 shown in FIGS. 1-6 positioned about body 358 of an ultrasonic dissector instrument 311. Such an instrument is disclosed in U.S. Pat. No. 6,024,750 which issued on Feb. 14, 2000 and is incorporated herein in its entirety by reference. As illustrated, cover 10 is preferably fastened to the distal end of elongated body 358 of instrument 311 proximally of a tool assembly 352 of instrument 311 such that when cover 10 is deployed, in the manner discussed above with respect to FIGS. 1-6, tool assembly 352 and/or contaminated or treated tissue is encompassed by cover 10 (FIG. 19).

While the invention has been particularly shown and described with reference to the preferred embodiments, it will be understood by those skilled in the art that various modifications and changes in form and detail may be made therein without departing from the scope and spirit of the invention. For example, a closure device other than an elastic band may be provided to close the cover about the tool assembly. For example, a drawstring "D" (FIG. 10) may be provided which can be grasped at the surgical site using graspers to close the cover 10 or the drawstring may be fed through the surgical instrument and be accessible from the proximal portion of the surgical instrument. Further, the cover need not be inverted about the tool assembly but rather may be slid directly over the tool assembly. Also, the cover may be configured to not only encompass the tool assembly but may also be configured to encompass a distal portion or the entire body portion of the surgical instrument. Accordingly, modifications such as those suggested above, but not limited thereto, are to be considered within the scope of the invention.

What is claimed is:

1. A surgical instrument for insertion into a body lumen comprising:
   an elongated body portion having an outer surface;
   a tool assembly supported on a distal end of the elongated body portion;
   a cover fitted about the elongated body portion, the cover movable from a first proximal position to a second position to cover a distal end of the tool assembly, the cover having a distal end secured to the elongated body portion adjacent the tool assembly; and
   a cover deployment member separable from the cover, the cover deployment member being positioned about the elongated body portion between the elongated body portion and the cover and being slidable in a distal direction along the body portion to move the cover to the second position.

2. A surgical instrument according to claim 1, wherein the cover deployment member is releasably engaged with the cover.

3. A surgical instrument according to claim 2, wherein the cover deployment member includes a sleeve slidably positioned about the body portion between a retracted position and an advanced position to move the cover from the first proximal position to the second position.

4. A surgical instrument according to claim 3, wherein the sleeve includes first and second half-sections, the first and second half-sections being urged into abutment with one another by at least one expandable member, the expandable member being expandable to permit the first and second half-sections to move outwardly with respect to each other.

5. A surgical instrument according to claim 4, wherein the expandable member is a resilient O-ring.

6. A surgical instrument according to claim 4, wherein the sleeve includes a proximally located annular ring dimensioned to facilitate movement of the sleeve between the retracted and advanced positions.

7. A surgical instrument according to claim 4, wherein the first sleeve half-section includes at least one projection and the second sleeve half-section includes at least one slot, the at least one projection being slidable into the at least one slot to maintain alignment between the first and second half-sections when the first and second half-sections move outwardly with respect to each other.

8. A surgical instrument according to claim 1, wherein the cover is fitted about the elongated body portion such that movement of the cover deployment member from the retracted position to the advanced position inverts the cover over the tool assembly.

9. A surgical instrument according to claim 1, wherein the cover deployment member includes a distal engagement member, a proximal guide portion and a central body portion interconnecting the engagement member and the guide portion, the cover deployment device being slidably supported on the elongated body portion to enable the cover deployment member to be moved to move the cover to the second position.

10. A surgical instrument according to claim 1, further including a closure device configured to enclose a proximal end of the cover after the cover is in the second position.

11. A surgical instrument according to claim 10, wherein the closure device includes an elastic band supported by the cover.

12. A surgical instrument according to claim 10, wherein the closure device includes a drawstring.

13. A surgical instrument according to claim 1, wherein the surgical instrument is a circular stapler.

14. A surgical instrument according to claim 1, wherein the surgical instrument is an ultrasonic dissector.

15. A surgical instrument according to claim 1, wherein surgical instrument is a linear stapler.

16. A surgical instrument according to claim 1, wherein the tool assembly includes a stationary shell having a plurality of staples.

17. A surgical instrument for insertion into a body lumen comprising:
   an elongated body portion;
   a tool assembly supported on a distal end of the elongated body portion;
   a cover having open proximal and distal ends and defining a lumen between the proximal and distal ends, the distal end of the cover attached to the surgical instrument adjacent a proximal end of the tool assembly, the cover being movable from a proximal position in which a portion of the elongated body portion is disposed within the lumen of the cover to a distal position in which the tool assembly of the surgical instrument is disposed within the lumen of the cover; and
   a cover deployment member having an annular engagement portion extending at least partially about the elongated body portion, the cover deployment member being slidable about the elongated body portion to engage and move the cover from the proximal position to the distal position.

18. A surgical instrument according to claim 17, wherein the cover deployment member is separable from the cover.

19. A surgical instrument for insertion into a body lumen comprising:
   an elongated body portion;
   a tool assembly supported on a distal end of the elongated body portion;
   a cover having open proximal and distal ends and defining a lumen between the proximal and distal ends, the distal end of the cover attached the surgical instrument adjacent a proximal end of the tool assembly, the cover being movable from a proximal position in which a portion of the elongated body portion is disposed within the lumen of the cover to a distal position in which the tool assembly of the surgical instrument is disposed within the lumen of the cover; and a cover deployment member having an annular engagement portion extending at least partially about the elongated body portion, the cover deployment member being slidable about the elongated body portion to engage and move the cover from the proximal position to the distal position, the cover deployment member including a first half-section and a second half-section coupled together by at least one expandable member such that the cover deployment member is movable between a contracted configuration and an expanded configuration, the annular engagement portion having a diameter less than the diameter of the tool assembly in the contracted configuration and a diameter greater than the diameter of the tool assembly in the expanded configuration, wherein the first and second half-sections of the annular engagement portion are configured to expand outwardly to the expanded configuration as the annular engagement portion rides over the tool assembly.

* * * * *